(12) United States Patent
Kim et al.

(10) Patent No.: US 10,683,261 B2
(45) Date of Patent: Jun. 16, 2020

(54) PHTHALONITRILE COMPOUND

(71) Applicant: LG CHEM, LTD., Seoul (KR)

(72) Inventors: Sang Woo Kim, Daejeon (KR); Seung Hee Lee, Daejeon (KR); Ki Ho Ahn, Daejeon (KR)

(73) Assignee: LG CHEM, LTD., Seoul (KR)

(*) Notice: Subject to any disclaimer, the term of this patent is extended or adjusted under 35 U.S.C. 154(b) by 141 days.

(21) Appl. No.: 15/576,009

(22) PCT Filed: Sep. 26, 2016

(86) PCT No.: PCT/KR2016/010748
§ 371 (c)(1),
(2) Date: Nov. 21, 2017

(87) PCT Pub. No.: WO2017/052323
PCT Pub. Date: Mar. 30, 2017

(65) Prior Publication Data
US 2018/0155276 A1 Jun. 7, 2018

(30) Foreign Application Priority Data
Sep. 24, 2015 (KR) .................. 10-2015-0135856

(51) Int. Cl.
*C07C 255/54* (2006.01)
*C07C 255/51* (2006.01)
(Continued)

(52) U.S. Cl.
CPC .......... *C07C 255/54* (2013.01); *C07C 255/33* (2013.01); *C07C 255/51* (2013.01);
(Continued)

(58) Field of Classification Search
CPC .................................................. C07C 255/54
(Continued)

(56) References Cited

U.S. PATENT DOCUMENTS 5,262,514 A * 11/1993 Keller .................... C08G 73/10
528/220
5,464,926 A * 11/1995 Keller ................ C08G 65/4012
528/125

(Continued)

FOREIGN PATENT DOCUMENTS

CN 101307013 A 11/2008
CN 101487190 A 7/2009
(Continued)

OTHER PUBLICATIONS

Derwent abstract, CN 102993070 A, to Wu et al. published Mar. 27, 2013 (Year: 2013).*

(Continued)

*Primary Examiner* — Jane L Stanley
(74) *Attorney, Agent, or Firm* — Dentons US LLP

(57) ABSTRACT

The present application can provide a phthalonitrile compound and a use thereof. The present application can provide a phthalonitrile compound capable of forming a phthalonitrile resin by self-curing or of serving as a curing agent after being mixed with another phthalonitrile compound, and a use of the phthalonitrile compound. The phthalonitrile compound can form a phthalonitrile resin by rapid self-curing even at a low temperature and does not create any defects resulting from the use of a conventional curing agent. Also, the phthalonitrile compound can be applied as a curing agent after being mixed with another compound, in which case, even if the content of the compound applied as a curing agent increases, the total content of the phthalonitrile resin obtained does not decrease, and thus a resin exhibiting an excellent degree of cure can be provided.

4 Claims, 3 Drawing Sheets

(51) Int. Cl.

| | | |
|---|---|---|
| *C07C 255/33* | (2006.01) | |
| *C07C 323/20* | (2006.01) | |
| *C09B 57/00* | (2006.01) | |
| *C09B 47/06* | (2006.01) | |
| *C08G 73/06* | (2006.01) | |
| *C08K 3/013* | (2018.01) | |
| *C07C 317/36* | (2006.01) | |
| *C07C 321/30* | (2006.01) | |
| *C07D 307/89* | (2006.01) | |
| *C08G 73/10* | (2006.01) | |
| *C08K 5/00* | (2006.01) | |
| *C09K 11/06* | (2006.01) | |

(52) U.S. Cl.
CPC .......... *C07C 317/36* (2013.01); *C07C 321/30* (2013.01); *C07C 323/20* (2013.01); *C07D 307/89* (2013.01); *C08G 73/0644* (2013.01); *C08G 73/10* (2013.01); *C08K 3/013* (2018.01); *C08K 5/0008* (2013.01); *C09B 47/063* (2013.01); *C09B 47/064* (2013.01); *C09B 57/00* (2013.01); *C09K 11/06* (2013.01); *C09K 2211/1007* (2013.01); *C09K 2211/1014* (2013.01)

(58) Field of Classification Search
USPC ........................................................ 524/600
See application file for complete search history.

(56) References Cited

U.S. PATENT DOCUMENTS

| 6,297,298 B1 | 10/2001 | Keller et al. | |
|---|---|---|---|
| 9,464,170 B2 * | 10/2016 | Keller | D01F 1/10 |
| 2015/0267022 A1 * | 9/2015 | Hu | C08J 9/14 |
| | | | 442/1 |
| 2018/0118666 A1 * | 5/2018 | Lee | C07C 255/51 |
| 2019/0276605 A1 * | 9/2019 | Ahn | C07C 255/54 |
| 2019/0284338 A1 * | 9/2019 | Kim | C08G 73/06 |

FOREIGN PATENT DOCUMENTS

| CN | 102993070 A | 3/2013 |
|---|---|---|
| CN | 103834008 A | 6/2014 |
| KR | 10-2001-0072625 A | 7/2001 |
| KR | 10-0558158 B1 | 2/2006 |
| WO | 00/00350 A1 | 1/2000 |

OTHER PUBLICATIONS

Derwent abstract, images, CN 102993070 A, to Wu et al. published Mar. 27, 2013 (Year: 2013).*
Derwent abstract, CN 101307013 A, to Ceng et al. published Nov. 19, 2008 (Year: 2008).*
EPO machine translation of CN 101307013 A, to Ceng et al. published Nov. 19, 2008 (Year: 2008).*
Derwent abstract images, CN 101307013 A, to Ceng et al. published Nov. 19, 2008 (Year: 2008).*
Xiang, et al.: "Synthesis and characterization of amide-containing phthalonitrile model compound", Polymer Materials Science and Engineering, Gaofenzi Cailiao Kexue Yu Gongcheng, vol. 29, No. 6, Jun. 2013, pp. 10-13.
Database CA: "Xiang, et al.: "Synthesis and characterization of amide-containing phthalonitrile model compound", XP009510349, Polymer Materials Science and Engineering, Gaofenzi Cailiao Kexue Yu Gongcheng, vol. 29, No. 6, Jun. 2013, pp. 10-13", XP002788589, Chemical Abstract Services, Columbus, Ohio, US.
Keller, Chapter 3. Study on Autocatalytic Curing Behavior of Phthalonitrile Derivatives, 1995.

* cited by examiner

[Figure 1]
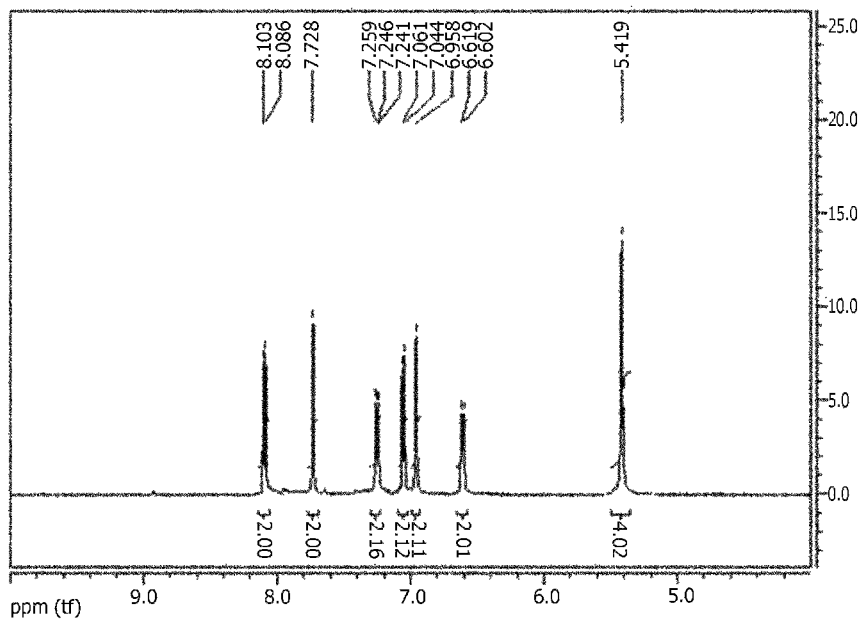
[Figure 2]
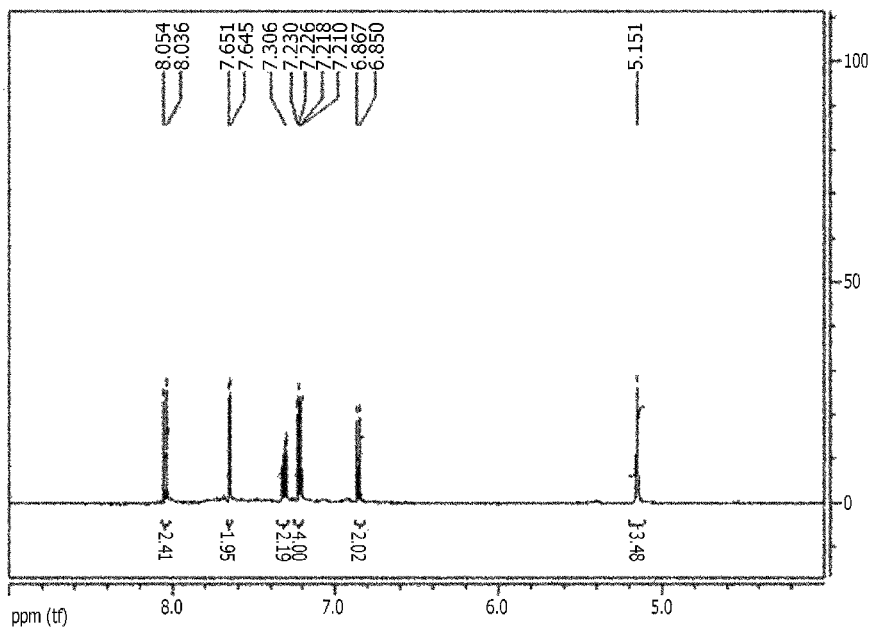

[Figure 3]
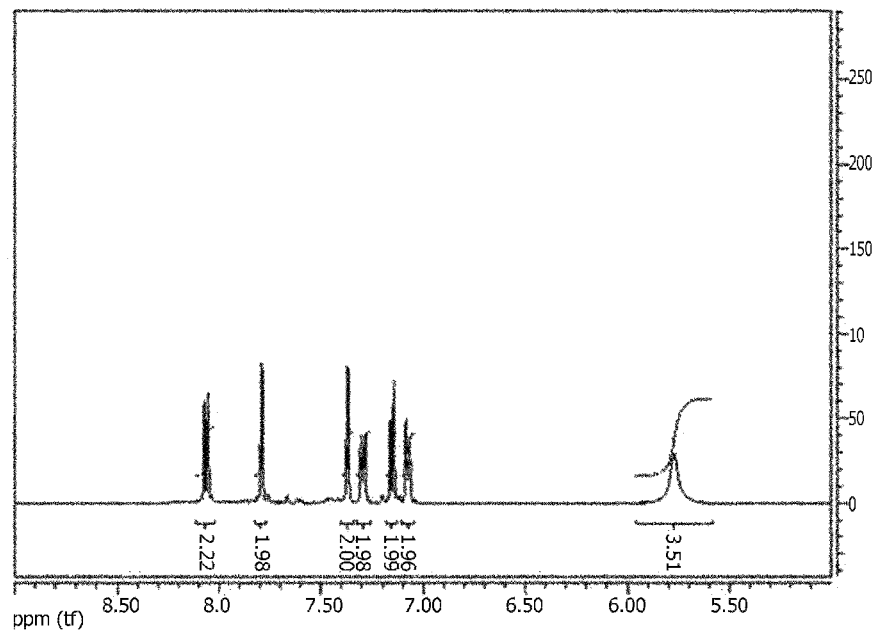
[Figure 4]
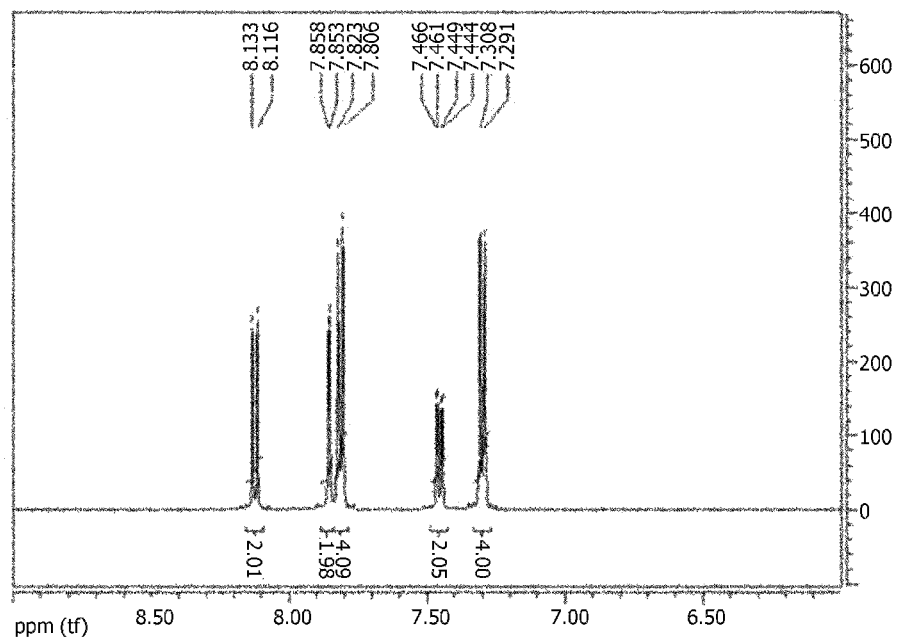

[Figure 5]
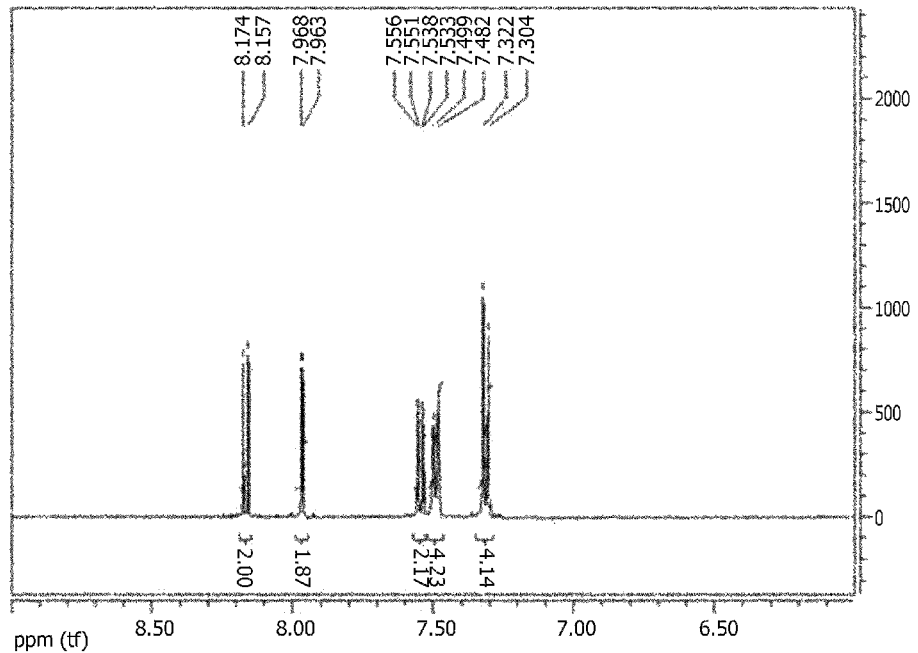
[Figure 6]
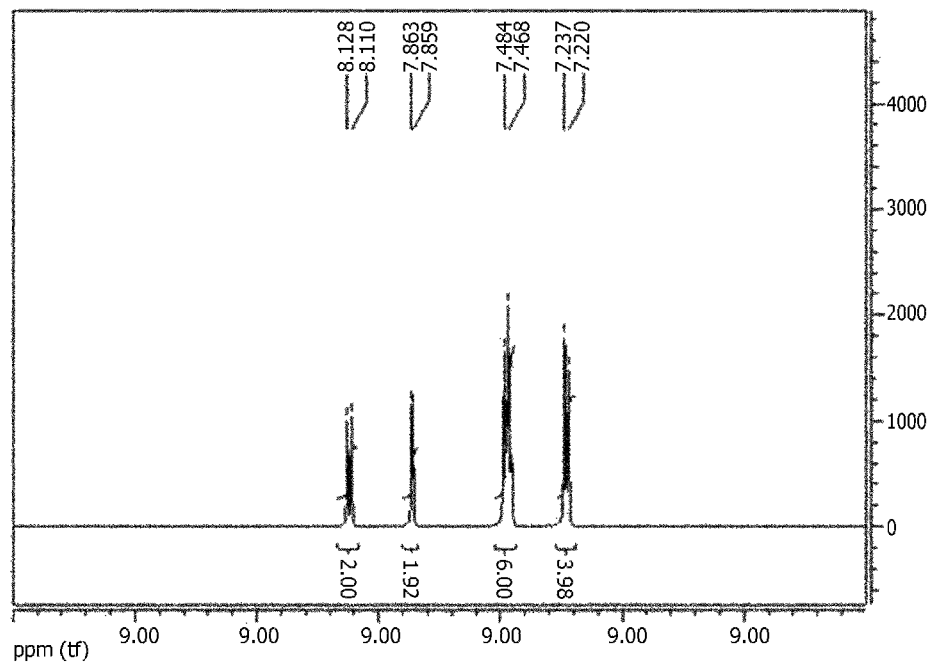

PHTHALONITRILE COMPOUND

CROSS-REFERENCE TO RELATED APPLICATIONS

This application is a National Stage Entry of International Application No. PCT/KR2016/010748 filed on Sep. 26, 2016, and claims the benefit of Korean Application No. 10-2015-0135856 filed on Sep. 24, 2015, all of which are hereby incorporated by reference in their entirety for all purposes as if fully set forth herein.

The present application relates to a phthalonitrile compound, a phthalonitrile resin, a polymerizable composition, a prepolymer, a composite, a precursor thereof, and a production method and use thereof.

TECHNICAL FIELD

Background Art

The phthalonitrile compound can be applied to various applications. For example, a phthalonitrile compound can be used as a raw material of a so-called phthalonitrile resin. For example, a composite formed by impregnating a phthalonitrile resin into a filler such as glass fiber or carbon fiber can be used as a material for automobiles, airplanes or ships. The process for producing the composite may include, for example, a process of mixing a mixture of phthalonitrile and a curing agent or a prepolymer formed by the reaction of the mixture with a filler and then curing the mixture (see, for example, Patent Document 1).

The other use of phthalonitrile compounds may include a use as precursors of phthalocyanine dyes. For example, a phthalonitrile compound may be compounded with a metal to be applied as a pigment.

The phthalonitrile compound can also be applied as a precursor of a fluorescent brightener or a photographic sensitizer or a precursor of an acid anhydride, and the like. For example, the phthalonitrile compound can be converted to an acid anhydride via an appropriate oxidation process and dehydration process, and such an acid anhydride can also be used as a precursor of polyamic acid or polyimide, and the like.

PRIOR ART DOCUMENT

Patent Document (Patent Document 1) Korean Patent No. 0558158

DISCLOSURE

Technical Problem

The present application can provide a novel phthalonitrile compound and a use thereof. As the use, precursors or raw materials of phthalonitrile resins, polymerizable compositions, prepolymers, composites, pigments, fluorescent brighteners, photo sensitizers or acid anhydrides can be exemplified.

Technical Solution

The present application relates to a phthalonitrile compound. The compound may be represented by Formula 1 below.

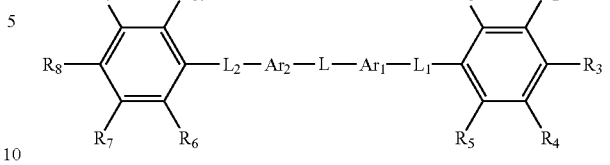

[Formula 1]

In Formula 1, $Ar_1$ and $Ar_2$ are each independently an aromatic divalent radical substituted with at least one amino group or hydroxy group, L, $L_1$ and $L_2$ are each independently a single bond, an alkylene group, an alkylidene group, an oxygen atom, a sulfur atom or $-S(=O)_2-$, and $R_1$ to $R_{10}$ are each independently hydrogen, an alkyl group, an alkoxy group, an aryl group or a cyano group, provided that at least two of $R_1$ to $R_5$ are a cyano group and at least two of $R_6$ to $R_{10}$ are a cyano group.

Here, $Ar_1$ and $Ar_2$ may be the same or different from each other, and L, $L_1$ and $L_2$ may be the same or different from one another.

In the present application, the term aromatic divalent radical may mean a divalent residue derived from benzene, a benzene-containing compound or any one derivative of the foregoing, unless otherwise specified. Here, the benzene-containing compound may mean a compound having a structure that two or more benzene rings are each condensed while sharing two carbon atoms, or linked by an appropriate linker. The aromatic divalent radical may contain, for example, 6 to 25, 6 to 20, 6 to 15 or 6 to 12 carbon atoms. In Formula 1, $Ar_1$ and $Ar_2$, which are an aromatic divalent radical, may be substituted with at least 1, 1 to 5, 1 to 4, 1 to 3 or 1 to 2 amino groups or hydroxy groups, and suitably may be substituted with an amino group. In some cases, the aromatic divalent radical may be optionally substituted by one or more substituents in addition to the amino group or the hydroxy group.

In one example, the aromatic divalent radical can be a radical derived from any one aromatic compound of Formulas 2 to 4 below.

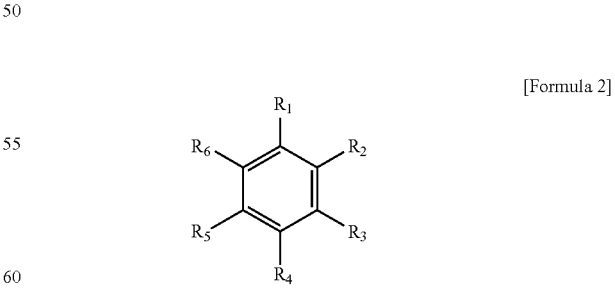

[Formula 2]

In Formula 2, $R_1$ to $R_6$ are each independently hydrogen, an alkyl group, an alkoxy group, an aryl group, a hydroxy group or an amino group, provided that at least two of $R_1$ to $R_6$ form radicals, and at least one of $R_1$ to $R_6$ is a hydroxy group or an amino group.

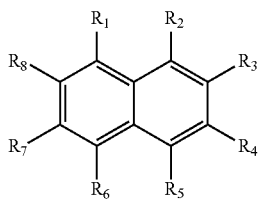

[Formula 3]

In Formula 3, $R_1$ to $R_8$ are each independently hydrogen, an alkyl group, an alkoxy group, an aryl group, a hydroxy group or an amino group, provided that at least two of $R_1$ to $R_8$ form radicals, and at least one of $R_1$ to $R_8$ is a hydroxy group or an amino group.

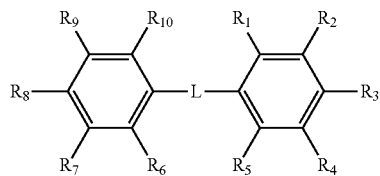

[Formula 4]

In Formula 4, $R_1$ to $R_{10}$ are each independently hydrogen, an alkyl group, an alkoxy group, an aryl group, a hydroxy group or an amino group, provided that at least two of $R_1$ to $R_{10}$ form radicals, L is an alkylene group, an alkylidene group, an oxygen atom or a sulfur atom, and at least one of $R_1$ to $R_{10}$ is a hydroxy group or an amino group.

$R_1$ to $R_6$ in Formula 2, $R_1$ to $R_8$ in Formula 3 or $R_1$ to $R_{10}$ in Formula 4 are each independently hydrogen, an alkyl group, an alkoxy group, an aryl group, a hydroxy group or an amino group, provided that at least two of these form radicals. Here, the formation of radicals may mean that the site is linked with another element of Formula 1. For example, in the case of $Ar_1$ in Formula 1, any one site of the radical-forming sites may be directly linked to $L_1$ in Formula 1 to form a covalent bond, and the other site may be directly linked to L in Formula 1 to form a covalent bond. In the case of $Ar_2$ in Formula 1, any one site of the radical-forming sites may be directly linked to $L_2$ in Formula 1 to form a covalent bond and the other site may be directly linked to L in Formula 1. At least one, 1 to 5, 1 to 4, 1 to 3 or 1 to 2 of the above respective substituents which form no radical may be an amino group or a hydroxy group and the remaining substituents may be hydrogen, an alkyl group or an alkoxy group; hydrogen or an alkyl group. In one example, in Formula 2, $R_1$ and $R_4$ or $R_1$ and $R_3$ may form the radicals. In this case, 1 to 3 or 1 to 2 of the substituents which form no radical may be an amino group or a hydroxy group, and the other substituents may be each independently hydrogen, an alkyl group, an alkoxy group or an aryl group; hydrogen, an alkyl group or an alkoxy group; or hydrogen or an alkyl group. Also, in Formula 3, any one of $R_1$, $R_6$, $R_7$ and $R_8$ and any one of $R_2$, $R_3$, $R_4$ and $R_5$ may form the radicals. In this case, 1 to 5, 1 to 4, 1 to 3 or 1 to 2 of the substituents which form no radical may be an amino group or a hydroxy group, and the other substituents may be each independently hydrogen, an alkyl group, an alkoxy group or an aryl group; hydrogen, an alkyl group or an alkoxy group; or hydrogen or an alkyl group. Also, in Formula 4, any one of $R_1$ to $R_5$ and any one of $R_6$ to $R_{10}$ may form the radicals. In this case, 1 to 5, 1 to 4, 1 to 3 or 1 to 2 of the substituents which form no radical may be an amino group or a hydroxy group, and the other substituents may be each independently hydrogen, an alkyl group, an alkoxy group or an aryl group; hydrogen, an alkyl group or an alkoxy group; or hydrogen or an alkyl group. Also, in Formula 4, L may be an alkylene group, an alkylidene group, an oxygen atom or a sulfur atom, and in another example, L may be an alkylene group, an alkylidene group or an oxygen atom, or an oxygen atom.

As a general example of $Ar_1$ or $Ar_2$ in Formula 1, an aromatic divalent radical of Formula 2 can be exemplified. In this case, the substituent at the meta-position or the para-position based on the substituent forming a covalent bond with L of Formula 1 among $R_1$ to $R_6$ in Formula 2 may be a hydroxy group or an amino group.

In the present application, the term alkyl group may be an alkyl group having 1 to 20 carbon atoms, 1 to 16 carbon atoms, 1 to 12 carbon atoms, 1 to 8 carbon atoms or 1 to 4 carbon atoms, unless otherwise specified. The alkyl group may be linear, branched or cyclic and may optionally be substituted with one or more substituents.

In the present application, the term alkoxy group may be an alkoxy group, having 1 to 20 carbon atoms, 1 to 16 carbon atoms, 1 to 12 carbon atoms, 1 to 8 carbon atoms or 1 to 4 carbon atoms, unless otherwise specified. The alkoxy group may be linear, branched or cyclic and may optionally be substituted with one or more substituents.

In the present application, the term aryl group may mean a monovalent residue derived from benzene, a compound comprising a benzene structure or any one derivative thereof as described in the item of the aromatic divalent radical, unless otherwise specified. The aryl group may comprise, for example, 6 to 25, 6 to 20, 6 to 15 or 6 to 12 carbon atoms. As a specific kind of the aryl group, a phenyl group, a benzyl group, a biphenyl group or a naphthalenyl group and the like can be exemplified, without being limited thereto. Also, in the scope of the aryl group in the present application, not only a functional group commonly referred to as an aryl group but also a so-called aralkyl group or arylalkyl group may be included.

In the present application, the term alkylene group or alkylidene group may mean an alkylene group or an alkylidene group, having 1 to 20 carbon atoms, 1 to 16 carbon atoms, 1 to 12 carbon atoms, 1 to 8 carbon atoms, or 1 to 4 carbon atoms, unless otherwise specified. The alkylene group or the alkylidene group may be linear, branched or cyclic. In addition, the alkylene group or the alkylidene group may be optionally substituted with one or more substituents.

As the substituent with which the alkyl group, alkoxy group, aryl group, aromatic divalent radical, alkylene group or alkylidene group in the present application may be optionally substituted, halogen such as chlorine or fluorine, an epoxy group such as a glycidyl group, an epoxyalkyl group, a glycidoxyalkyl group or an alicyclic epoxy group, an acryloyl group, a methacryloyl group, an isocyanate group, a thiol group, an alkyl group, an alkoxy group or an aryl group can be exemplified, but is not limited thereto.

In Formula 1, L, $L_1$ and $L_2$ may be a single bond, an alkylene group, an alkylidene group, an oxygen atom, a sulfur atom or —S(=O)$_2$—.

In one example, L of Formula 1 may be a single bond, an alkylene group or an alkylidene group, or —S(=O)$_2$—. The alkylene group or the alkylidene group may be optionally substituted with at least one halogen atom or haloalkyl group, that is, an alkyl group substituted with a halogen atom, and in some cases, may be optionally substituted with a substituent other than a halogen atom. Furthermore, the term single bond in the above is a case where no separate atom exists in the corresponding site, and for example, if L is a single bond, a structure in which $Ar_1$ and $Ar_2$ are directly linked can be derived.

In Formula 1, $L_1$ and $L_2$ may be an alkylene group, an alkylidene group or an oxygen atom, and in one example, may be an oxygen atom.

In Formula 1, $R_1$ to $R_{10}$ are each independently hydrogen, an alkyl group, an alkoxy group, an aryl group or a cyano group, provided that at least two of $R_1$ to $R_5$ are a cyano group and at least two of $R_6$ to $R_{10}$ are a cyano group. In another example, $R_1$ to $R_{10}$, which are no cyano group, may be each independently hydrogen, an alkyl group or an alkoxy group; or hydrogen or an alkyl group. In one example, any two of $R_2$ to $R_4$ and any two of $R_7$ to $R_9$ in Formula 1 may be a cyano group, and the remaining substituents may be each independently hydrogen, an alkyl group, an alkoxy group or an aryl group; hydrogen, an alkyl group or an alkoxy group; or hydrogen or an alkyl group.

The compound of Formula 1 can be effectively used in various applications in which so-called phthalonitrile compounds are known to be applicable. For example, the phthalonitrile compound can be effectively used as a raw material or precursor capable of producing a so-called phthalonitrile resin. The compound may exhibit a low melting temperature, have excellent reactivity with a curing agent and exhibit a wide process window to be effectively applied to the application. The compound may be used as a precursor of a dye such as a phthalocyanine dye or a precursor or a raw material of a fluorescent brightener, a photographic sensitizer or an acid anhydride, and the like, in addition to the above applications.

The compound of Formula 1 can be synthesized by a known synthesis method of an organic compound. For example, the compound of Formula 1 can be synthesized by a method of reacting an aromatic compound substituted with an amino group or a hydroxy group, while having a phenolic hydroxy group, and an aromatic compound having at least two cyano groups (ex. nitro displacement method), and the like. In the field of organic chemistry, the aromatic compounds capable of forming the structure of the compound of Formula 1 are known, and such a compound can be all applied to the production of the above compounds in consideration of the desired structure.

The present application also relates to a use of the compound. As the use of the compound, a raw material or a precursor of a phthalonitrile resin, a phthalocyanine dye, a fluorescent brightener, a photographic sensitizer or an acid anhydride can be exemplified, as described above.

As one example of the use, for example, the present application may be directed to a phthalonitrile resin. The phthalonitrile resin may contain a polymerized unit derived from the compound of the Formula 1. In the present application, the term polymerized unit derived from a certain compound may mean a skeleton of a polymer formed by polymerization or curing of the compound.

In the phthalonitrile resin, the polymerized unit of the compound of Formula 1 may be a polymerized unit which is formed by a reaction of the above compound with a curing agent, a reaction between the compounds of Formula 1 or a reaction of the compound of Formula 1 with another phthalonitrile compound.

The compound of Formula 1 may contain an amino group or a hydroxy group which autonomously reacts with a cyano group to form a polymerized unit without any separate curing agent. Therefore, the phthalonitrile resin can be formed only by the compound of Formula 1, and if necessary, the compound of Formula 1 can be used as a curing agent for other phthalonitrile monomers or compositions containing the same. In this case, since the compound of Formula 1 itself participates in the reaction and becomes a component of the phthalonitrile resin, the curing rate and the curing density can be increased and even if the content of the compound of Formula 1 serving as a curing agent, the physical properties do not deteriorate.

When the phthalonitrile resin is formed by using only the compound of the Formula 1 or by applying the phthalonitrile other than the compound of the Formula 1 together with the compound of the Formula 1, a curing agent is not required as described above, but in some cases, other suitable curing agents may also be mixed and used.

Also, the phthalonitrile resin may further comprise a polymerized unit of other phthalonitrile compounds in addition to the polymerized unit of the compound of Formula 1. In this case, the kind of the phthalonitrile compound capable of being selected and used is not particularly limited and the known compounds known to be useful for forming the phthalonitrile resin and controlling its physical properties can be applied. As an example of such a compound, compounds disclosed in U.S. Pat. Nos. 4,408,035, 5,003,039, 5,003,078, 5,004,801, 5,132,396, 5,139,054, 5,208,318, 5,237,045, 5,292,854, or 5,350,828 can be exemplified, but is not limited thereto.

As described above, if necessary, a curing agent may be used together with the compound of Formula 1, where the kind of the curing agent is not particularly limited as long as it is generally used for forming a phthalonitrile resin. Such a curing agent is known in various documents including the above-described US patents.

In one example, an amine compound such as an aromatic amine compound or a hydroxy compound can be used as a curing agent. In the present application, the hydroxy compound may mean a compound containing at least one or two hydroxy groups in the molecule.

The present application also relates to a polymerizable composition. The polymerizable composition may comprise the compound of Formula 1. The polymerizable composition is capable of forming a so-called phthalonitrile resin, and basically comprises the compound of Formula 1, and may or may not further comprise a curing agent. That is, as described above, the compound of Formula 1 can be autonomously subjected to the curing reaction, and thus the polymerizable composition may not contain an amine compound or a hydroxy compound, serving as a curing agent. That is, the polymerizable composition may not contain a compound having an amine group or a hydroxyl group in addition to the compound of the Formula 1.

If necessary, an appropriate curing agent may be included, where as the curing agent contained in the polymerizable composition, for example, a curing agent as described above may be used. When the curing agent is included, the ratio of the curing agent in the polymerizable composition is not particularly limited. The ratio can be adjusted so that the desired curability can be ensured, for example, in consideration of the ratio or kind of the curable component such as the compound of the Formula 1 contained in the composition. For example, the curing agent may be included in an amount of about 0.02 to 2 moles or 0.02 to 1.5 moles per mole of the compound of Formula 1 contained in the polymerizable composition. However, the above ratios are only examples of the present application. Usually, if the ratio of the curing agent in the polymerizable composition is high, the process window tends to be narrowed, whereas if the ratio of the curing agent is low, the curability tends to become insufficient, so that the suitable ratio of the curing agent can be selected in consideration of this point.

In another example, the polymerizable composition may comprise a phthalonitrile compound other than the compound of Formula 1. As described above, in the above case, the compound of Formula 1 may serve as a curing agent. In this case, even when the content of the compound of the Formula 1 serving as a curing agent is increased, the content of the phthalonitrile resin is not reduced and a resin of high cure degree can be obtained. When the compound of the Formula 1 as a curing agent is contained in the polymerizable composition together with other phthalonitrile compounds, the ratio thereof is not particularly limited and it may be included, for example, within a range of 2% by mole to 95% by mole in the total composition.

The polymerizable composition comprising the compound of Formula 1 can be quickly and easily cured even at a low temperature, for example a temperature of up to about 350° C., and can exhibit a low melting temperature. In addition, when the compound of the Formula 1 is contained as a curing agent as described above and the ratio thereof becomes excessive, the compound of the Formula 1 participates in the reaction and the constituents of the final product (phthalonitrile resin and the like), so that deterioration of physical properties can be prevented.

The polymerizable composition may further comprise various additives, including other phthalonitrile compounds and the like, in addition to the compound of the Formula 1. As an example of such an additive, various fillers can be exemplified. The kind of the material that can be used as the filler is not particularly limited, and any known suitable filler may be used depending on the intended uses. As the exemplary filler, a metal material, a ceramic material, glass, a metal oxide, a metal nitride or a carbon-based material, and the like can be exemplified, but is not limited thereto. Furthermore, the type of the filler is not particularly limited as well and may be various forms, such as fibrous materials such as aramid fibers, glass fibers, carbon fibers or ceramic fibers, or woven fabrics, nonwoven fabrics, strings or cords, formed by the materials, particulates comprising nanoparticles, polygons or other amorphous forms. Here, as the carbon-based materials, graphite, graphene or carbon nanotubes, and the like, or derivatives or isomers such as oxides thereof, and the like can be exemplified. However, the components that the polymerizable composition may further comprise are not limited to the above, and various monomers known to be applicable to the production of so-called engineering plastics such as polyimide, polyamide or polystyrene, or other additives may also be included without limitation, depending on the purpose.

The present application also relates to a prepolymer formed by reaction of the polymerizable composition, that is, the polymerizable composition comprising the compound of Formula 1.

In the present application, the term prepolymer state may mean a state where the compound of Formula 1 and the curing agent in the polymerizable composition are in a state polymerized in a certain degree (for example, a state that polymerization of a so-called stage A or B step occurs), without reaching a completely polymerized state, and exhibit an appropriate fluidity, for example, allow to process a composite to be described below.

The prepolymer may also exhibit excellent curability and low melting temperature as described above.

The prepolymer may further comprise any known additives in addition to the above components. As the example of such an additive, the above-described fillers and the like can be exemplified, but is not limited thereto.

The present application also relates to a composite. The composite may comprise the above-described phthalonitrile resin and filler. As described above, it is possible to achieve excellent curability, a low melting temperature and a wide process window through the compound of the Formula 1 of the present application, and accordingly, a so-called reinforced resin composite (reinforced polymer composite) with excellent physical properties comprising various fillers can be easily formed. The composite thus formed may comprise the phthalonitrile resin and filler and may be applied to, for example, various applications, including durables such as automobiles, airplanes or ships, and the like.

The kind of the filler is not particularly limited and may be suitably selected in consideration of the intended use. The specific types of the usable fillers are as described above.

Also, the ratio of the filler is not particularly limited, and may be set in an appropriate range depending on the intended use.

The present application also relates to a precursor for producing the composite, wherein the precursor may comprise, for example, the polymerizable composition and the filler as described above, or the prepolymer and the filler as described above.

The composite can be prepared in a known manner using the precursor. For example, the composite can be formed by curing the precursor.

In one example, the precursor may be prepared by blending the polymerizable composition, which is prepared by compounding the compound of Formula 1 described above with a curing agent in a molten state, or the prepolymer, with the filler in a state molten by heating or the like. For example, the above-described composite can be prepared by molding the precursor thus produced into a desired shape and then curing it. The polymerizable composition or prepolymer has a low melting temperature and a wide process temperature together with excellent curability, so that molding and curing can be efficiently performed in the above process.

In the above processes, the method for forming the prepolymer or the like, the method for producing the composite by compounding such a prepolymer with the filler, and processing and curing it, and the like may be carried out according to known methods.

The present application may also be directed to a precursor of a phthalocyanine dye, a precursor of a fluorescent brightener or a precursor of a photographic sensitizer, comprising the compound, or an acid anhydride derived from the compound. The method for forming the precursor or the method for producing the acid anhydride, using the compound, is not particularly limited and all known methods capable of producing the precursor or acid anhydride using phthalonitrile compounds can be applied.

Advantageous Effects

The present application can provide a phthalonitrile compound which can be autonomously cured to form a phthalonitrile resin or can be combined with other phthalonitrile compounds to serve as a curing agent, and a use thereof.

The phthalonitrile compound can be self-cured at a high speed even at a low temperature to form a phthalonitrile resin and does not cause defects due to the use of existing curing agents.

Also, the phthalonitrile compound can be applied as a curing agent by being blended with another compound, and in this case, even when the content of the compound to be applied as a curing agent is increased, the content of the entire phthalonitrile resin is not decreased, whereby a resin of excellent cure degree can be provided.

BRIEF DESCRIPTION OF DRAWINGS

FIGS. 1 to 6 are each NMR analysis results for the compounds prepared in Preparation Examples 1 to 6.

MODE FOR INVENTION

The phthalonitrile resins of the present application and the like will be specifically described by way of Examples and Comparative Examples, but the scope of the resins and the like is not limited to the following examples.

1. Nuclear Magnetic Resonance (NMR) Analysis

The NMR analysis was performed according to the manufacturer's manual using a 500 MHz NMR instrument from Agilent. A sample for NMR measurement was prepared by dissolving the compound in DMSO (dimethyl sulfoxide)-d6.

2. DSC (Differential Scanning Calorimetry) Analysis

The DSC analysis was performed in $N_2$ flow atmosphere, while raising the temperature from 35° C. to 450° C. at a rate of temperature increase of 10° C./min with a Q20 system from TA instrument.

3. TGA (Thermogravimetric Analysis) Analysis

The TGA analysis was performed using a TGA e850 instrument from Mettler-Toledo. In the case of the compounds prepared in Preparation Examples, they were analyzed in N2 flow atmosphere, while raising the temperature from 25° C. to 800° C. at a rate of temperature increase of 10° C./min.

Preparation Example 1. Synthesis of Compound (PN1)

The compound (PN1) of Formula A below was synthesized in the following manner. 54.9 g of the compound of Formula B below and 150 g of DMF (dimethyl formamide) were put into a 3 neck RBF (round bottom flask), stirred at room temperature and dissolved. Subsequently, 51.9 g of the compound of Formula C below was added thereto, and 50 g of DMF was added thereto, and then the mixture was stirred and dissolved. Subsequently, 62.2 g of potassium carbonate and 50 g of DMF were added thereto together and the mixture was reacted in a state where the temperature was raised to 85° C. with stirring, and then cooled to room temperature. The cooled reaction solution was poured into 0.2N hydrochloric acid aqueous solution to be neutralized and precipitated, followed by filtering and then washing with water. Thereafter, the filtered reactant was dried in a vacuum oven at 100° C. for 1 day, and after removal of water and residual solvent, the compound of Formula A below was obtained in a yield of about 85% by weight. The NMR results for the compound of Formula A were described in FIG. 1.

[Formula A]

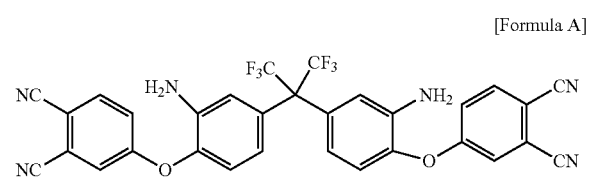

[Formula B]

[Formula C]

Preparation Example 2. Synthesis of Compound (PN2)

The compound (PN2) of Formula D below was synthesized in the following manner. 32.4 g of the compound of Formula E below and 130 g of DMF (dimethyl formamide) were put into a 3 neck RBF (round bottom flask), stirred at room temperature and dissolved. Subsequently, 51.9 g of the compound of Formula C in Preparation Example 1 above was added thereto, and 50 g of DMF was added thereto, and then the mixture was stirred and dissolved. Subsequently, 62.2 g of potassium carbonate and 50 g of DMF were added thereto together and the temperature was raised to 85° C. with stirring. The mixture was reacted in this state for about 5 hours, and then cooled to room temperature. The cooled reaction solution was poured into 0.2N hydrochloric acid aqueous solution to be neutralized and precipitated, followed by filtering and then washing with water. Thereafter, the filtered reactant was dried in a vacuum oven at 100° C. for 1 day, and after removal of water and residual solvent, the compound of Formula D below was obtained in a yield of about 80% by weight. The NMR results for the compound of Formula D were described in FIG. 2.

[Formula D]

[Formula E]

Preparation Example 3. Synthesis of Compound (PN3)

The compound (PN3) of Formula F below was synthesized in the following manner. 42 g of the compound of Formula G below and 200 g of DMF (dimethyl formamide) were put into a 3 neck RBF (round bottom flask), stirred at room temperature and dissolved. Subsequently, 51.9 g of the compound of Formula C in Preparation Example 1 above was added thereto, and 50 g of DMF was added thereto, and then the mixture was stirred and dissolved. Subsequently, 62.2 g of potassium carbonate and 50 g of DMF were added thereto together and the temperature was raised to 85° C. with stirring. The mixture was reacted in this state for about 5 hours, and then cooled to room temperature. The cooled reaction solution was poured into 0.2N hydrochloric acid aqueous solution to be neutralized and precipitated, followed by filtering and then washing with water. Thereafter, the filtered reactant was dried in a vacuum oven at 100° C. for 1 day, and after removal of water and residual solvent, the compound of Formula F below was obtained in a yield of about 82% by weight. The NMR results for the compound of Formula F were described in FIG. 3.

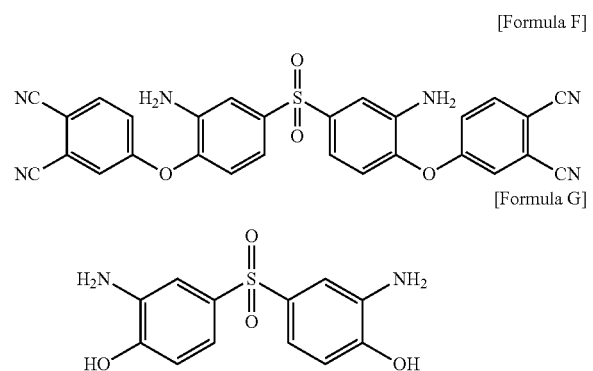

[Formula F]

[Formula G]

Preparation Example 4. Synthesis of Compound (PN4)

The compound (PN4) of Formula H below was synthesized in the following manner. 27.9 g of the compound of Formula I below and 100 g of DMF (dimethyl formamide) were put into a 3 neck RBF (round bottom flask), stirred at room temperature and dissolved. Subsequently, 51.9 g of the compound of Formula C in Preparation Example 1 above was added thereto, and 50 g of DMF was added thereto, and then the mixture was stirred and dissolved. Subsequently, 62.2 g of potassium carbonate and 50 g of DMF were added thereto together and the temperature was raised to 85° C. with stirring. The mixture was reacted in this state for about 5 hours, and then cooled to room temperature. The cooled reaction solution was poured into 0.2N hydrochloric acid aqueous solution to be neutralized and precipitated, followed by filtering and then washing with water. Thereafter, the filtered reactant was dried in a vacuum oven at 100° C. for 1 day, and after removal of water and residual solvent, the compound of Formula H below was obtained in a yield of about 83% by weight. The NMR results for the compound of Formula H were described in FIG. 4.

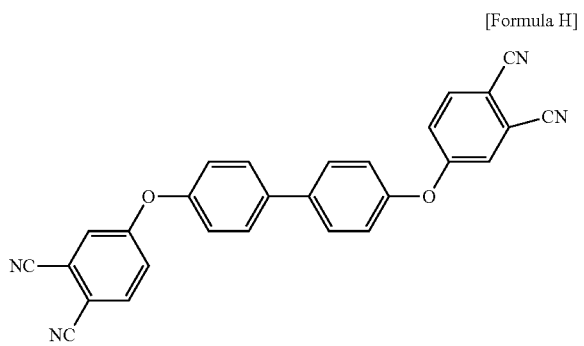

[Formula H]

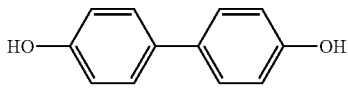

[Formula I]

Preparation Example 5. Synthesis of Compound (PN5)

50.4 g of the compound of Formula K below and 150 g of DMF (dimethyl formamide) were put into a 3 neck RBF (round bottom flask), stirred at room temperature and dissolved. Subsequently, 51.9 g of the compound of Formula C in Preparation Example 1 above was added thereto, and 50 g of DMF was added thereto, and then the mixture was stirred and dissolved. Subsequently, 62.2 g of potassium carbonate and 50 g of DMF were added thereto together and the temperature was raised to 85° C. with stirring. The mixture was reacted in this state for about 5 hours, and then cooled to room temperature. The cooled reaction solution was poured into 0.2N hydrochloric acid aqueous solution to be neutralized and precipitated, followed by filtering and then washing with water. Thereafter, the filtered reactant was dried in a vacuum oven at 100° C. for 1 day, and after removal of water and residual solvent, the compound (PN5) of Formula J below was obtained in a yield of about 87% by weight. The NMR results for the compound of Formula J were described in FIG. 5.

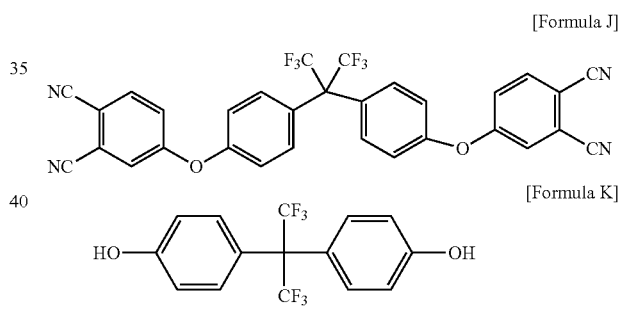

[Formula J]

[Formula K]

Preparation Example 6. Synthesis of Compound (PN6)

The compound of Formula L below was synthesized in the following manner. 32.7 g of the compound of Formula M below and 120 g of DMF (dimethyl formamide) were put into a 3 neck RBF (round bottom flask), stirred at room temperature and dissolved. Subsequently, 51.9 g of the compound of Formula C in Preparation Example 1 above was added thereto, and 50 g of DMF was added thereto, and then the mixture was stirred and dissolved. Subsequently, 62.2 g of potassium carbonate and 50 g of DMF were added thereto together and the temperature was raised to 85° C. with stirring. The mixture was reacted in this state for about 5 hours, and then cooled to room temperature. The cooled reaction solution was poured into 0.2N hydrochloric acid aqueous solution to be neutralized and precipitated, followed by filtering and then washing with water. Thereafter, the filtered reactant was dried in a vacuum oven at 100° C. for 1 day, and after removal of water and residual solvent, the compound (PN6) of Formula L below was obtained in a yield of about 80% by weight. The NMR results for the compound of Formula L were described in FIG. 5.

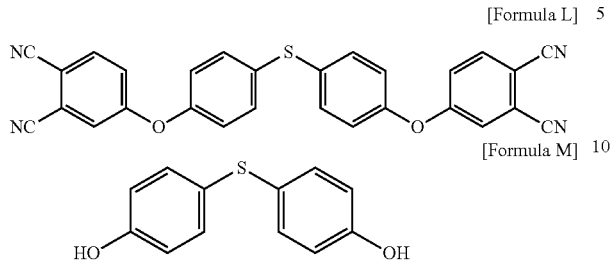

Preparation Example 7. Synthesis of Compound (CA)

As the compound (CA) of Formula N below, a commercial product from TCI (Tokyo Chemical Industry Co., Ltd.) was purchased and used without further purification.

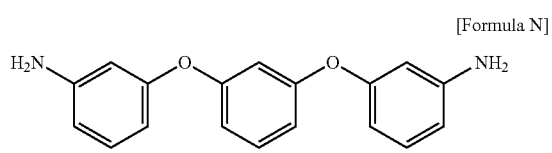 [SMILES: Nc1cccc(Oc2cccc(Oc3cccc(N)c3)c2)c1]

Example 1

The exothermal onset temperature and exothermal maximum temperature of the compound (PN1) of Preparation Example 1 were confirmed through the DSC analysis. In addition, the residue at Td 10% and 800° C. was confirmed through the TGA analysis for the material in which the compound (PN1) of Preparation Example 1 was cured at 240° C. for 2 hours using an IR curing oven.

Example 2

The exothermal onset temperature and exothermal maximum temperature of the compound (PN2) of Preparation Example 2 were confirmed through the DSC analysis. In addition, the residue at Td 10% and 800° C. was confirmed through the TGA analysis for the material in which the compound (PN2) of Preparation Example 2 was cured at 240° C. for 2 hours using an IR curing oven.

Example 3

The exothermal onset temperature and exothermal maximum temperature of the compound (PN3) of Preparation Example 3 were confirmed through the DSC analysis. In addition, the residue at Td 10% and 800° C. was confirmed through the TGA analysis for the material in which the compound (PN3) of Preparation Example 3 was cured at 240° C. for 2 hours using an IR curing oven.

Example 4

The compound (PN1) of Preparation Example 1 and the compound (PN4) of Preparation Example 4 were mixed so that the compound (PN1) of Preparation Example 1 was present in about 0.2 moles per mole of the compound (PN4) of Preparation Example 4. Then, the exothermal onset temperature and the exothermal maximum temperature of the mixture were confirmed through the DSC analysis. In addition, the residue at Td 10% and 800° C. was confirmed through the TGA analysis for the material in which the mixture was cured at 240° C. for 2 hours using an IR curing oven.

Example 5

The compound (PN1) of Preparation Example 1 and the compound (PN5) of Preparation Example 5 were mixed so that the compound (PN1) of Preparation Example 1 was present in about 0.2 moles per mole of the compound (PN5) of Preparation Example 5. Then, the exothermal onset temperature and the exothermal maximum temperature of the mixture were confirmed through the DSC analysis. In addition, the residue at Td 10% and 800° C. was confirmed through the TGA analysis for the material in which the mixture was cured at 240° C. for 2 hours using an IR curing oven.

Example 6

The compound (PN1) of Preparation Example 1 and the compound (PN6) of Preparation Example 6 were mixed so that the compound (PN1) of Preparation Example 1 was present in about 0.2 moles per mole of the compound (PN6) of Preparation Example 6. Then, the exothermal onset temperature and the exothermal maximum temperature of the mixture were confirmed through the DSC analysis. In addition, the residue at Td 10% and 800° C. was confirmed through the TGA analysis for the material in which the mixture was cured at 240° C. for 2 hours using an IR curing oven.

Comparative Example 1

The exothermal onset temperature and exothermal maximum temperature of the compound (PN4) of Preparation Example 4 were confirmed through the DSC analysis. In addition, the residue at Td 10% and 800° C. was confirmed through the TGA analysis for the material in which the compound (PN4) of Preparation Example 4 was cured at 240° C. for 2 hours using an IR curing oven.

Comparative Example 2

The exothermal onset temperature and exothermal maximum temperature of the compound (PN5) of Preparation Example 5 were confirmed through the DSC analysis. In addition, the residue at Td 10% and 800° C. was confirmed through the TGA analysis for the material in which the compound (PN5) of Preparation Example 5 was cured at 240° C. for 2 hours using an IR curing oven.

Comparative Example 3

The exothermal onset temperature and exothermal maximum temperature of the compound (PN6) of Preparation Example 6 were confirmed through the DSC analysis. In addition, the residue at Td 10% and 800° C. was confirmed through the TGA analysis for the material in which the compound (PN6) of Preparation Example 6 was cured at 240° C. for 2 hours using an IR curing oven.

Comparative Example 4

The compound (PN4) of Preparation Example 4 and the compound (CA) of Preparation Example 7 were mixed so that the compound (CA) of Preparation Example 7 was present in about 0.2 moles per mole of the compound (PN4) of Preparation Example 4. Then, the exothermal onset temperature and the exothermal maximum temperature of the mixture were confirmed through the DSC analysis. In addition, the residue at Td 10% and 800° C. was confirmed through the TGA analysis for the material in which the mixture was cured at 240° C. for 2 hours using an IR curing oven.

Comparative Example 5

The compound (PN5) of Preparation Example 5 and the compound (CA) of Preparation Example 7 were mixed so that the compound (CA) of Preparation Example 7 was present in about 0.2 moles per mole of the compound (PN5) of Preparation Example 5. Then, the exothermal onset temperature and the exothermal maximum temperature of the mixture were confirmed through the DSC analysis. In addition, the residue at Td 10% and 800° C. was confirmed through the TGA analysis for the material in which the mixture was cured at 240° C. for 2 hours using an IR curing oven.

Comparative Example 6

The compound (PN6) of Preparation Example 6 and the compound (CA) of Preparation Example 7 were mixed so that the compound (CA) of Preparation Example 7 was present in about 0.2 moles per mole of the compound (PN6) of Preparation Example 6. Then, the exothermal onset temperature and the exothermal maximum temperature of the mixture were confirmed through the DSC analysis. In addition, the residue at Td 10% and 800° C. was confirmed through the TGA analysis for the material in which the mixture was cured at 240° C. for 2 hours using an IR curing oven.

The measurement results of Examples and Comparative Examples above were summarized and described in Table 1 below.

TABLE 1

| | | Exothermal Onset Temperature | Exothermal Maximum Temperature | Td 10% | Residue at 800° C. |
|---|---|---|---|---|---|
| Example | 1 | 255 | 261 | 472 | 59.6 |
| | 2 | 238 | 245 | 444 | 69 |
| | 3 | 166 | 194 | 369 | 60.2 |
| | 4 | 258 | 265 | 502 | 70 |
| | 5 | 260 | 268 | 473 | 58.6 |
| | 6 | 248 | 256 | 479 | 63.7 |
| Comparative Example | 1 | — | — | 455 | 20.2 |
| | 2 | — | — | 422 | 7.3 |
| | 3 | — | — | 430 | 6.4 |
| | 4 | 279 | 283 | 508 | 69.5 |
| | 5 | 358 | 376 | 496 | 60.4 |
| | 6 | 301 | 304 | 478 | 63.4 |

In Table 1, first, comparing the results of Examples 1 to 3 and Comparative Examples 1 to 3, curing peaks in the case of Examples 1 to 3 where each was even in a state of a single compound were confirmed so that exothermal onset temperatures and the exothermal maximum temperatures could be confirmed, whereas in Comparative Examples 1 to 3, no curing peak could be confirmed even in a state where the temperature was raised to 450° C. Also, in the case of Examples 1 to 3, as a result of curing in the IR curing oven, cross-linking reaction occurred even within a relatively short time (2 hours), so that the residue at 800° C. was 60 to 70% and exhibited high heat resistance, but in the case of Comparative Examples 1 to 3, even after being maintained in the curing oven, the residue at 800° C. was in a level of 6 to 20%.

In the case of Examples 4 to 6, which were the mixtures of the compounds of Comparative Examples 1 to 3 and the compound of Example 1, respectively, it could be seen from the result of confirming DSC that the curing of the compounds of Comparative Examples 1 to 3, in which the curing reaction did not proceed alone, occurred, whereby the residue at 800° C. was greatly improved to 60 to 70%.

On the other hand, comparing the results of Comparative Examples 4 to 6 and Examples 4 to 6, it was confirmed that the curing in Examples 4 to 6, to which the compound (PN1) of Preparation Example 1 was applied, was initiated at a lower temperature over Comparative Examples 4 to 6 to which the compound (CA) of Preparation Example 7 as the known curing agent was applied, whereby it could be seen that Examples 4 to 6 exhibited more excellent rapid curability.

From these results, it can be seen that self-curability can be ensured through the use of the compound of the present invention, thereby avoiding the void problem or the like which occurs when a mono-molecular curing agent or the like is introduced. In addition, it is possible to secure a higher cure degree by preventing the decrease of the monomer ratio or the like due to the content of the curing agent from the above characteristics, thereby expecting an improved result even in terms of thermal and mechanical properties and increasing the productivity through reduction of the process time by lowering the curing temperature and shortening the curing time.

The invention claimed is:

1. A phthalonitrile resin comprising polymerized units derived from a compound of Formula 1 below:
    wherein the polymerized unit is formed by a reaction of the compound of Formula 1 with a curing agent, a reaction between compounds of Formula 1, a reaction of the compound of Formula 1 with another phthalonitrile compound, or a reaction of the compound of Formula 1 with a curing agent and another phthalonitrile compound:

[Formula 1]

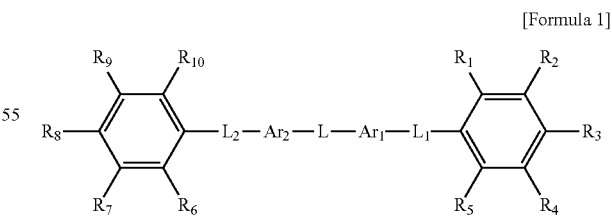

wherein, $Ar_1$ and $Ar_2$ are each independently an aromatic divalent radical substituted with at least one amino group or hydroxy group, L, $L_1$ and $L_2$ are each independently a single bond, an alkylene group, an alkylidene group, an oxygen atom, a sulfur atom or —S(=O)$_2$—, and $R_1$ to $R_{10}$ are each independently hydrogen, an alkyl group, an alkoxy group, an aryl group or a cyano group, provided that at least two of $R_1$ to $R_5$ are a cyano group and at least two of $R_6$ to $R_{10}$ are a cyano group, wherein the aromatic divalent radical in Formula 1 is a divalent radical derived from an aromatic compound represented by at least one or Formula 3 or Formula 4 below:

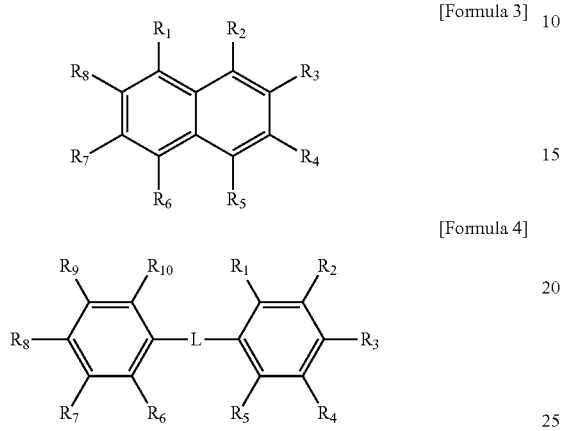

[Formula 3]

[Formula 4]

wherein, $R_1$ to $R_8$ of Formula 3 are each independently hydrogen, an alkyl group, an alkoxy group, an aryl group, a hydroxy group or an amino group, provided that at least two of $R_1$ to $R_8$ form radicals, and at least one of $R_1$ to $R_8$ is a hydroxy group or an amino group, wherein, $R_1$ to $R_{10}$ of Formula 4 are each independently hydrogen, an alkyl group, an alkoxy group, an aryl group, a hydroxy group or an amino group, provided that at least two of $R_1$ to $R_{10}$ form radicals, L is an alkylene group, an alkylidene group, an oxygen atom or a sulfur atom, and at least one of $R_1$ to $R_{10}$ is a hydroxy group or an amino group.

2. The pthalonitrile resin according to claim 1, wherein L in Formula 1 is a single bond, an alkylene group, an alkylene group substituted with a halogen atom, an alkylidene group, an alkylidene group substituted with a halogen atom, or —S(=O)$_2$—.

3. The pthalonitrile resin according to claim 1, wherein $L_1$ and $L_2$ in Formula 1 are an oxygen atom.

4. A composite comprising the phthalonitrile resin of claim 1 and a filler.

* * * * *